United States Patent [19]

White

[11] 4,034,884

[45] July 12, 1977

[54] BIOLOGICAL SPECIMEN PROCESS APPARATUS AND COVER MEMBER THEREFOR

[75] Inventor: Fred K. White, Glen Ellyn, Ill.

[73] Assignee: Miles Laboratories, Inc., Elkhart, Ind.

[21] Appl. No.: 560,557

[22] Filed: Mar. 20, 1975

[51] Int. Cl.² .......................................... B65D 41/18
[52] U.S. Cl. .................................. 220/8; 220/306; 220/355
[58] Field of Search .............. 220/8, 306, 307, 355, 220/356, 352, 353

[56] References Cited

U.S. PATENT DOCUMENTS

| 1,450,674 | 4/1923 | Marston | 220/8 |
| 1,707,841 | 4/1929 | Broadfoot | 220/8 |
| 1,934,138 | 11/1933 | Paul et al. | 220/8 |
| 2,727,651 | 12/1955 | Mickelson | 220/306 |
| 3,149,747 | 9/1964 | Burgess | 220/306 |
| 3,189,072 | 6/1965 | Starr | 220/306 |
| 3,516,572 | 6/1970 | Davis | 220/306 |
| 3,872,996 | 3/1975 | Dogliotti | 220/306 |
| Re. 28,165 | 9/1974 | McCormick | 425/17 |

FOREIGN PATENT DOCUMENTS

| 118,416 | 12/1969 | Norway | 220/307 |
| 474,228 | 8/1969 | Switzerland | 220/306 |

Primary Examiner—William Price
Assistant Examiner—Joseph Man-Fu Moy
Attorney, Agent, or Firm—Louis E. Davidson

[57] ABSTRACT

Container apparatus for processing biological specimens therein is described wherein a perforated box-like bottom member has a perforated box-like cover member telescopically fitted thereon which is capable of being supported in several positions to adjust the enclosed volume of the container to compensate for different sized specimens. The unique cover member is also separately described.

10 Claims, 4 Drawing Figures

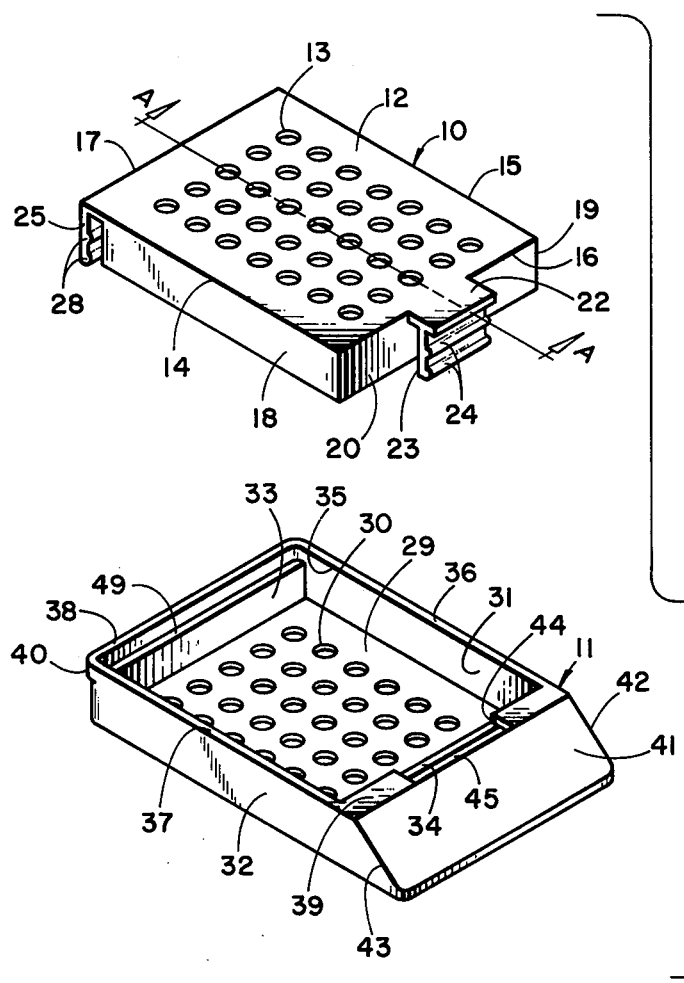
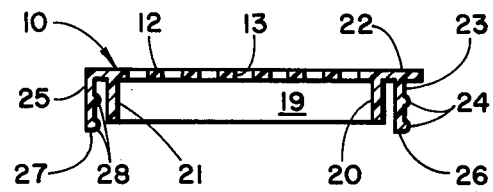
FIG. 1
FIG. 2
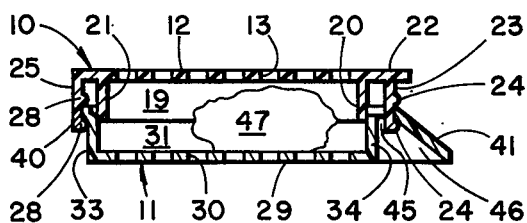
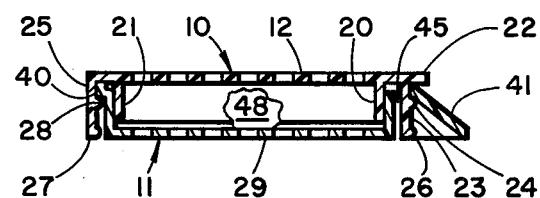
FIG. 3
FIG. 4

BIOLOGICAL SPECIMEN PROCESS APPARATUS AND COVER MEMBER THEREFOR

BACKGROUND AND PRIOR ART

It is well known in the art that biological tissues can be sliced into thin sections on a microtome for subsequent microscopic examination by a pathologist, for example. In order to prepare the specimen for such slicing it must first be processed with several fluids to dehydrate the tissue, to clear the tissue with a suitable oil and then to infiltrate the tissue with a paraffin wax or a combination of wax and resinous material. This processing has been conveniently carried out by placing the specimen in a fluid-permeable capsule and successively submerging the capsule in the necessary fluids. The resulting processed specimen is then removed from the capsule and embedded in a block of paraffin wax for subsequent mounting in a microtome for slicing.

Generally the capsule apparatus employed for the tissue processing is separate from the apparatus employed for embedding the specimen in paraffin. U.S. Pat. No. 3,674,396 (now U.S. Reissue Pat No. 28,165)describes improved apparatus wherein an open- -topped box-like perforated mold member having a perforated removable cover can be used with the cover in place as a tissue processing capsule and with cover removed can be used for embedding a specimen in paraffin. The apparatus described in the above prior art patent had the disadvantage that the volume of the processing apparatus could not be adjusted to compensate for different sized specimens. There is a commercial need for combination processing-embedding apparatus that is adjustable for such different sized specimens. There is also a commercial need for an adjustable cover to be used with the apparatus of the above prior art patent.

SUMMARY OF THE INVENTION

In accordance with the present invention, biological specimen processing container apparatus of adjustable size is provided comprising in combination an open-topped, rectangular box-like base member having a perforated bottom wall and an open-bottomed rectangular box-like cover member having a perforated top wall, said cover member being telescopically interfitted with said box-like base member, said base and cover members being movable telescopically between first and second operative positions, and abutment means on said base member and said cover member, said abutment means being interengageable in a first relationship when said base and cover members are in said first operative position to hold said members in said first operative position, and said abutment means also being interengageable in a second relationship when said base and cover members are in said second operative position to hold said members in said second operative position.

Further in accordance with the present invention a cover member adapted for telescopic cooperation with an open-topped rectangular box-like base member having external abutment means and a perforated bottom wall to provide therewith biological specimen processing container apparatus of adjustable size is provided comprising an open-bottomed, rectangular box-like member having a perforated top wall, said box-like member being formed at opposite sides thereof with detent members of generally L-shaped cross -section which project outwardly and thence downwardly from adjacent said top wall, said detent members each being formed with at least one protrusion thereon.

DESCRIPTION OF THE DRAWINGS

FIG. 1 is a perspective view of the separate parts of the biological specimen processing apparatus in exploded relation;

FIG. 2 is a vertical cross-sectional view taken along plane A—A of FIG. 1 and through the cover member only;

FIG. 3 is a vertical cross-sectional view taken along plane A—A of FIG. 1 and showing the cover and base members in one operative position to accommodate a large specimen in the apparatus; and FIG. 4 is a vertical cross-sectional view similar to FIG. 3 showing the cover and base members in another operative position to accommodate a smaller specimen in the apparatus.

DESCRIPTION OF THE INVENTION

Referring to FIGS. 1 to 3, the novel cover member 10 is capable of being removably attached to an open-topped box-like base member 11 to form a biological specimen processing container. The cover member 10 has a generally flat rectangular top wall 12 with a plurality of perforations 13 therein. Top wall 12 has longitudinal edges 14 and 15 and transverse edges 16 and 17. Opposing parallel longitudinal sidwalls 18 and 19 depend from the longitudinal edges 14 and 15 of top wall 12. Transverse sidewall 20 depends from transverse edge 16 of top wall 12, while opposing parallel transverse sidewall 21 depends from top wall 12 and is spaced inward from transverse edge 17 of top wall 12. Sidewalls 18, 19, 20 and 21 form an open-bottomed rectangular box-like structure. A tab 22 extends from the midpoint of transverse edge 16 of top wall 12 coplanar with top wall 12. A tongue 23 depends from tab 22 and extends to end 26 below the plane of the lower edges of sidewalls 18, 19, 20 and 21. Tongue 23 has a plurality of protrusions spaced therealong and directed outwardly of cover member 10. Preferably these protrusions are parallel transverse ribs 24 on the outer surface threof. A latch member 25 extends outwardly and thence downwardly from transverse edge 17 of top wall 12 and terminates in end 27 below the plane of the lower edges of sidewalls 18, 19, 20 and 21. The ends 26 and 27 of tongue 23 and latch member 25 are coplanar. Latch member 25 has a plurality of protrusions spaced along the inner surface thereof. Preferably these protrusions are parallel transverse ribs 28. Tab 22 and tongue 23 form in combination one detent member and latch member 25 forms another detent member. Both detent members are of generally L-shaped cross-section and project outwardly and thence downwardly from adjacent the top wall 12. The protrusions 24 and 28 also form abutments.

The open-topped box-like base member 11 is formed in a generally rectangular shape with a bottom wall 29 having a plurality of perforations 30 therein, opposing parallel longitudinal sidewalls 31 and 32 and opposing parallel transverse endwalls 33 and 34 extending upward from bottom wall 29. Sidewalls 31 and 32 and endwalls 33 and 34 have coplanar upper edge surfaces 36, 37, 38 and 39, respectively, which are normal to said sidewalls and endwalls and which form a substantially flat annular end surface defining the open top 35.

The outer face of the transverse endwall 33 is formed along its upper edge with an outwardly projecting ridge 40 which is conveniently formed as an offset 49 in endwall 33. Connected to and extending downwardly and outwardly from the upper edge portion 39 of the transverse endwall 34 is a slanted wall 41, and the adjacent end portions of the longitudinal sidewalls 31 and 32 extend outwardly beyond the transverse endwall 34 to join the slanted wall 41 along slant edges 42 and 43, respectively. The upper edge portion 39 of the transverse endwall 34 is cut away as at 44 to form a transverse slot 45 which affords access to the transverse chamber 46 of generally triangular cross-section which is formed between the outer face of endwall 34 and the underside of the slanted wall 41. The ridge 40 and the portion of the slanted wall at the margin of slot 45 each form abutment means.

In order to utilize the apparatus of this invention, a biological specimen 47 is placed within the base member 11 as shown in FIG. 3. The cover member 10 is then removably telescopically fitted within the open top 35 of base member 11 and at the same time inserting the tongue 23 of the cover member 10 through the slot 45 of base member 11 to the position shown in FIG. 3 wherein the lowermost rib 24 is located below and the uppermost rib 24 is located above the edge portion of the slanted wall 41 at the margin of slot 45 and said edge portion is engaged by the outer surface portion of tongue 23 located between the ribs 24. The portion of the slanted wall at the margin of the slot 45 thus forms an engaging means associated with transverse endwall 34 which is adapted for abutting engagement with at least one of the ribs 24. As the cover member 10 is moved toward its operative position shown in FIG. 3, the lowermost rib 28 on the latch member 25 is snapped over the ridge 40 of base member 11 so that the ridge 40 is accommodated between the uppermost and lowermost ribs 28. The ridge 40 thus forms an engaging means associated with transverse endwall 33 which is in abutting engagement with at least one of the ribs 28.

The first operative position of the cover member 10 shown in FIG. 3 is to accommodate a relatively large specimen 47. The cross-sectional dimensions of the perforations 13 of cover member 10 and of the perforations 30 of base member 11 are both smaller than any corresponding dimensions of the specimen 47 so that the specimen will be retained within the so-formed processing container apparatus. The fluid-permeable container apparatus containing the specimen can then be successively placed in solutions of dehydrating agents, clearing agents and paraffin wax to properly prepare the specimen for subsequent embedding in paraffin. The processing fluids easily pass through the perforations 13 and 30.

The cover member 10 is then removed from base member 11 by lifting up on tab 22 to disengage tongue 23 from slot 45 and to disengage latch member 25 from ridge 40. Base member 11 and specimen 47 can then be subsequently handled in a well-known manner described in U.S. Reissue Pat. No. 28,165 to embed the specimen in paraffin.

When a smaller specimen 48 is employed, the cover member 10 can be adjusted to a second operative position with respect to base member 11 as is shown in FIG. 4. Tongue 23 is depressed through slot 45 until the uppermost rib 24 engages the underside of the portion of the slanted wall 41 at the margin of said slot and said wall portion is located between said uppermost rib 24 and the tab 22. At the same time the latch member 25 is depressed to snap the uppermost rib 28 over the ridge 40 so that ridge 40 is located between the uppermost rib 28 and the top wall 12. In this arrangement ends 26 and 27 of tongue 23 and latch member 25, respectively are substantially coplanar with the bottom surface of bottom wall 29 of base member 11.

Cover member 10 and base member 11 are preferably each individually formed as unitary members from organoplastics such as polyethylene, polypropylene, polystyrene, styrene-acrylonitrile copolymers, polycarbonate, acetal copolymers, nitrile-acrylonitrile-styrene copolymers, polymethylpentene, polyacrylate, polymeth-acrylate, copolymers of trioxane and formaldehyde and the like. The cover member 10 is preferably formed from a copolymer of trioxane and formaldehyde. Base member 11 is also preferably formed from a copolymer of trioxane and formaldehyde.

In a laboratory handling a large number of specimens, it is necessary that proper specimen identification be maintained. Slanted wall 41 of member 11 is employed for this purpose. When base member 11 is formed from the above preferred material, it can be easily written upon with pencil or pen for the application of an identification designation to the slanted wall 41.

In summary, this invention relates to a specific cover member that can be used with biological specimen processing apparatus and to an improved adjustable processing container that is formed when such cover member is so used.

What is claimed is:

1. A biological specimen processing container apparatus of adjustable size comprising in combination an open-topped, rectangular box-like base member having a perforated bottom wall and an open-bottomed rectangular box-like cover member having a perforated top wall, two opposing parallel longitudinal sidewalls and two opposing parallel transverse endwalls, said cover member being telescopically interfitted with said box-like base member, said base and cover members being movable telescopically between first and second operative positions, and abutment means on said base member and said cover member, said abutment means being interengageable in a first relationship when said base and cover members are in said first operative position to hold said members in said first operative position, and said abutment means also being interengageable in a second relationship when said base and cover members are in said second operative position to hold said members in said second operative position, said abutment means on said cover member being provided by detent members formed on opposite sides of said cover member, said detent members being of generally L-shaped cross-section and projecting outwardly and thence downwardly from adjacent said top wall, said detent members each being formed with at least one protrusion thereon for said interengagement with said abutment means on said base member.

2. Apparatus according to claim 1 wherein the base member and the cover member are each individually formed as unitary members from organoplastics.

3. A cover member adapted for telescopic cooperation with an open-topped rectangular box-like base member having external abutment means and a perforated bottom wall to provide therewith biological specimen processing container apparatus of adjustable size, said cover member comprising an open-bottomed, rectangular box-like member having a perforated top wall, two opposing parallel longitudinal sidewalls and two opposing parallel transverse endwalls, said box-like member being formed at opposite sides thereof with detent members of generally L-shaped cross-section which project outwardly and thence downwardly from adjacent said top wall, said detent members each being formed with at least one protrusion thereon.

4. A cover member according to claim 3 which is formed as a unitary member from organoplastics.

5. A cover member according to claim 3 wherein one of said detent members is formed as a tab extending from one edge of the top wall generally coplanar with said top wall and having a tongue depending therefrom and formed with a plurality of protrusions spaced therealong.

6. A cover member according to claim 3 wherein said detent member protrusions are formed as parallel transverse ribs.

7. Biological specimen processing container apparatus according to claim 1 wherein one of said detent members is formed as a tab extending from one edge of and generally coplanar with said top wall, there being a tongue depending from said tab and formed with a plurality of protrusions spaced therealong.

8. Biological specimen processing container apparatus according to claim 1 wherein said protrusions are formed as parallel ribs.

9. Bilogical specimen processing container apparatus according to claim 7 wherein said protrusions are formed as parallel ribs extending transversely across said tongue.

10. A biological specimen processing apparatus of adjustable size comprising in combination an open-topped, rectangular box-like base member having a perforated bottom wall and an open-bottomed rectangular box-like cover member having a perforated top wall, two opposing parallel longitudinal sidewalls and two opposing parallel transverse endwalls, wherein the open-topped rectangular box-like base member having a perforated bottom wall has two opposing parallel longitudinal sidewalls and two opposing parallel transverse endwalls extending upward from said bottom wall, said base member also having a slanted wall with an exterior surface capable of being easily written upon extending downwardly and outwardly from the upper surface of one of the transverse endwalls, the two longitudinal sidewalls extending beyond said transverse endwall to join said slanted wall to form a transverse chamber between said transverse endwall, said slanted wall and said extensions of said longitudinal sidewalls, said base member also having a transverse slot located along the junction between the slanted wall and the upper surface of the transverse endwall, said transverse slot providing upper access to said transverse chamber, said base member further having an outwardly projecting ridge along the outer surface of the other transverse endwall and communication with the upper surface of said endwall, and wherein the open-bottomed rectangular box-like cover member having a perforated top wall has first and second detent members formed at opposite ends thereof, said detent members being of generally L-shaped cross-section which project outwardly and thence downwardly from adjacent said top wall, said detent members each being formed with at least one protrusion thereon, the cover member of said apparatus being removably attached to said base member with the first detent member of said cover member being inserted through the transverse slot of said base member and with the second detent member of said cover member being placed over the outwardly projecting ridge of said base member, said cover member telescopically fitting within said base member, said cover member being supported in several positions with respect to said base member, in each of such positions an edge of the transverse slot of the base member is abutting a protrusion of the first detent member of the cover member and the projecting ridge of the base member is correspondingly abutting a protrusion of the second detent member of the cover member.

* * * * *